(12) United States Patent
Zhao et al.

(10) Patent No.: US 7,112,419 B2
(45) Date of Patent: Sep. 26, 2006

(54) HUMAN HEPATOMA ASSOCIATED PROTEIN AND THE POLYNUCLEOTIDE ENCODING SAID POLYPEPTIDE

(75) Inventors: Xintai Zhao, Shanghai (CN); Dafang Wan, Shanghai (CN); Jianren Gu, Shanghai (CN)

(73) Assignee: Shanghai Cancer Institute, Shanhgai (CN)

( * ) Notice: Subject to any disclaimer, the term of this patent is extended or adjusted under 35 U.S.C. 154(b) by 248 days.

(21) Appl. No.: 10/257,124

(22) PCT Filed: Apr. 17, 2001

(86) PCT No.: PCT/CN01/00559

§ 371 (c)(1),
(2), (4) Date: Oct. 8, 2002

(87) PCT Pub. No.: WO01/85775

PCT Pub. Date: Nov. 15, 2001

(65) Prior Publication Data

US 2003/0148331 A1    Aug. 7, 2003

(30) Foreign Application Priority Data

Apr. 17, 2000   (CN) ................................ 00 1 15401

(51) Int. Cl.
*C12P 21/06* (2006.01)
(52) U.S. Cl. .................... 435/69.1; 530/350; 536/23.1; 536/23.5; 536/24.33; 435/320.1; 435/325
(58) Field of Classification Search ................ 530/350; 536/23.5, 23.1, 24.3, 24.33; 435/320.1, 325, 435/69.1; 514/2, 44; 424/277.1
See application file for complete search history.

(56) References Cited

FOREIGN PATENT DOCUMENTS

WO   WO 96/27609    2/1996
WO   WO 00/37492    6/2000

OTHER PUBLICATIONS

Zhao et al. GenEMBL Database Accession No. AF246287 (Apr. 1, 2001; Version AF242687.1; GI: 13491870); pp. 2.*
Bendig (Genet. Eng. 1988; (7) 91-127).*
Ferrari et al. (Clin. Exp. Immunol. 2003; 132: 1-8).*
Patterson AP. Memorandum (Jan. 14, 2003); pp. 3.*
Pandha et al. (Current Opinion in Investigational Drugs 2000; 1 (1): 122-134).*
Amalfitano et al. (Current Gene Therapy 2002, 2: 111-133).*
Verma et al. (Nature 1997, 389: 239-242).*
De Plaen et al. (Immunogenetics. 1994; 40: 360-369).*
Skolnick et al. (Trends in Biotechnology 2000; 18: 34-39).*
Bowie et al. (Science 257: 1306-1310, 1990).*
Saijo et al. (Cancer Sci. Oct. 2004; 95 (10): 772-776).*
Kelland (Eur. J. Cancer. Apr. 2004; 40 (6): 827-836).*
Bergers et al. (Current Opinion in Genetics and Development. 2000; 10: 120-127).*
Gura (Science. 1997; 278: 1041-1042).*

* cited by examiner

*Primary Examiner*—Stephen L. Rawlings
(74) *Attorney, Agent, or Firm*—Dorsey & Whitney LLP

(57) ABSTRACT

The invention relates to a new kind of human protein associated with hepatoma and the polynucleotide encoding the polypeptide and a process for producing the polypeptide by recombinant methods. The present invention also relates to a method of applying the polypeptide for the diagnosis and treatment of various kinds of disease, such as cancer. Further, present invention relates to the antagonist of the polypeptide and therapeutic use of the same. In addition, the invention relates to the use of the same. In addition, the invention relates to the use of polynucleotide encoding the hepatoma associated human protein.

12 Claims, 2 Drawing Sheets

Figure 1:
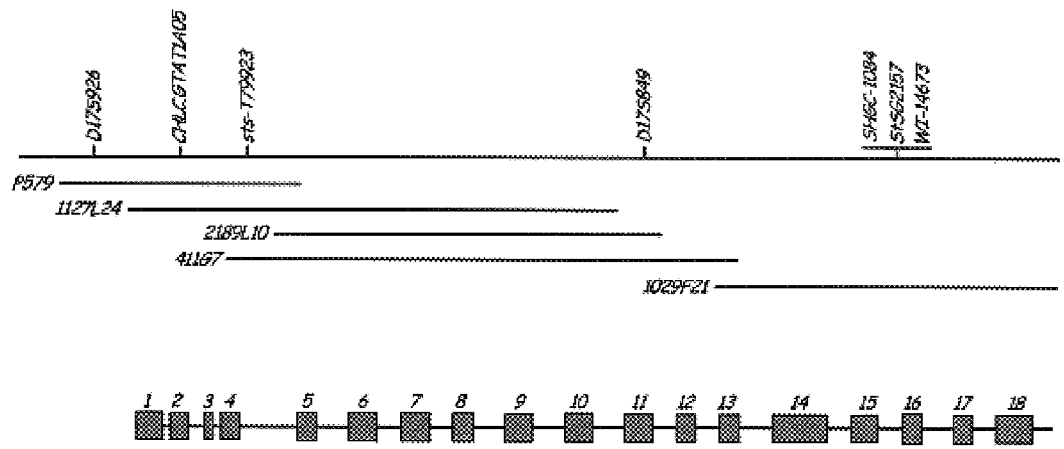

SEQUENCE LISTING

<160> NUMBER OF SEQ ID NOS: 18

<210> SEQ ID NO 1
<211> LENGTH: 2078
<212> TYPE: DNA
<213> ORGANISM: Homo sapiens

```
<220> FEATURE:
<221> NAME/KEY: CDS
<222> LOCATION: (56)..(2077)

<400> SEQUENCE: 1
cggggaggcc tgagttgggc tcgcggcggg ggtcggcagg gggccgggtg gcgga atg        58
                                                              Met
                                                                1 atg gag gag gag gaa ctg gag ttc gtg gag gag ctg gaa gcc gtg ctg        106
Met Glu Glu Glu Glu Leu Glu Phe Val Glu Glu Leu Glu Ala Val Leu
      5                  10                  15 cag ctc acg ccc gag gtg cag ctg gcc atc gag cag gtg ttt cca agc        154
Gln Leu Thr Pro Glu Val Gln Leu Ala Ile Glu Gln Val Phe Pro Ser
 20                  25                  30 cag gac cct cta gat cga gca gat ttc aat gct gtt gag tat atc aat        202
Gln Asp Pro Leu Asp Arg Ala Asp Phe Asn Ala Val Glu Tyr Ile Asn
 35                  40                  45 acc ctg ttc cca acc gag caa tct ctg gcg aac ata gac gaa gtc gtg        250
Thr Leu Phe Pro Thr Glu Gln Ser Leu Ala Asn Ile Asp Glu Val Val
 50                  55                  60                  65 aac aaa att agg ctg aaa ata agg aga ctg gat gac aat att cga act        298
Asn Lys Ile Arg Leu Lys Ile Arg Arg Leu Asp Asp Asn Ile Arg Thr
                 70                  75                  80 gtt gta aga ggt cag acg aac gtg ggg cag gat gga cgg caa gcg ctt        346
Val Val Arg Gly Gln Thr Asn Val Gly Gln Asp Gly Arg Gln Ala Leu
             85                  90                  95 gaa gag gct cag aaa gct atc caa caa ctc ttt ggc aaa atc aaa gat        394
Glu Glu Ala Gln Lys Ala Ile Gln Gln Leu Phe Gly Lys Ile Lys Asp
        100                 105                 110 atc aaa gac aaa gct gaa aaa tca gag caa atg gtg aaa gaa atc acc        442
Ile Lys Asp Lys Ala Glu Lys Ser Glu Gln Met Val Lys Glu Ile Thr
115                 120                 125 cgt gat att aag caa tta gat cac gcc aaa cgc cac ctg acc acc tca        490
Arg Asp Ile Lys Gln Leu Asp His Ala Lys Arg His Leu Thr Thr Ser
130                 135                 140                 145 atc acc aca ctg aac cac ctg cac atg ctg gca gga ggt gtc gac tcc        538
Ile Thr Thr Leu Asn His Leu His Met Leu Ala Gly Gly Val Asp Ser
                150                 155                 160 ctc gaa gcc atg acc agg cga aga caa tac gga gaa gtt gct aat ctc        586
Leu Glu Ala Met Thr Arg Arg Arg Gln Tyr Gly Glu Val Ala Asn Leu
            165                 170                 175 ctt cag ggt gtg atg aat gtc ctg gag cac ttc cac aag tat atg ggg        634
Leu Gln Gly Val Met Asn Val Leu Glu His Phe His Lys Tyr Met Gly
        180                 185                 190 att ccg cag atc cgg cag ctt tcc gaa aga gtg aag gct gca cag act        682
Ile Pro Gln Ile Arg Gln Leu Ser Glu Arg Val Lys Ala Ala Gln Thr
    195                 200                 205 gag tta gga cag caa atc ctg gca gat ttt gaa gaa gcg ttt cct tcc        730
Glu Leu Gly Gln Gln Ile Leu Ala Asp Phe Glu Glu Ala Phe Pro Ser
210                 215                 220                 225 cag ggc acc aag aga cca gga gga ccc agc aat gtt cta cga gat gca        778
Gln Gly Thr Lys Arg Pro Gly Gly Pro Ser Asn Val Leu Arg Asp Ala
                230                 235                 240 tgt ctg gtt gct aat att cta gat ccc agg atc aaa cag gaa atc atc        826
Cys Leu Val Ala Asn Ile Leu Asp Pro Arg Ile Lys Gln Glu Ile Ile
            245                 250                 255 aaa aag ttt att aaa cag cat ctg tca gag tat ctg gta ctt ttt caa        874
Lys Lys Phe Ile Lys Gln His Leu Ser Glu Tyr Leu Val Leu Phe Gln
        260                 265                 270
```

```
gaa aac caa gat gtt gcc tgg ctg gac aaa atc gac aga cgc tat gcc      922
Glu Asn Gln Asp Val Ala Trp Leu Asp Lys Ile Asp Arg Arg Tyr Ala
    275                 280                 285 tgg ata aaa cgc cag ctt gtg gac tat gag gag aaa tac ggc cgc atg      970
Trp Ile Lys Arg Gln Leu Val Asp Tyr Glu Glu Lys Tyr Gly Arg Met
290                 295                 300                 305 ttt cca cgt gag tgg tgc atg gct gag agg att gcg gtg gaa ttt tgc     1018
Phe Pro Arg Glu Trp Cys Met Ala Glu Arg Ile Ala Val Glu Phe Cys
                310                 315                 320 cat gtg aca agg gca gaa ctt gcc aag att atg cgt acc aga gcg aag     1066
His Val Thr Arg Ala Glu Leu Ala Lys Ile Met Arg Thr Arg Ala Lys
            325                 330                 335 gaa att gaa gtg aaa ttg ctt ctt ttt gct att caa aga aca act aac     1114
Glu Ile Glu Val Lys Leu Leu Leu Phe Ala Ile Gln Arg Thr Thr Asn
        340                 345                 350 ttt gag ggg ttt ctt gca aaa cgc ttc tcc ggc tgc acc ctg acc gat     1162
Phe Glu Gly Phe Leu Ala Lys Arg Phe Ser Gly Cys Thr Leu Thr Asp
    355                 360                 365 ggg acc ctg aaa aag ctt gag tct cca ccc cca tct acc aat ccc ttc     1210
Gly Thr Leu Lys Lys Leu Glu Ser Pro Pro Pro Ser Thr Asn Pro Phe
370                 375                 380                 385 ctg gaa gat gag cca aca cca gag atg gag gaa ctg gca acg gag aaa     1258
Leu Glu Asp Glu Pro Thr Pro Glu Met Glu Glu Leu Ala Thr Glu Lys
                390                 395                 400 gga gat tta gat caa cca aag aag cct aaa gcc cca gac aat cca ttt     1306
Gly Asp Leu Asp Gln Pro Lys Lys Pro Lys Ala Pro Asp Asn Pro Phe
            405                 410                 415 cat ggc att gtt tcc aag tgt ttt gag cct cat ctc tac gtg tat atc     1354
His Gly Ile Val Ser Lys Cys Phe Glu Pro His Leu Tyr Val Tyr Ile
        420                 425                 430 gaa tcc caa gac aag aac ctc gga gag ctg ata gat cgg ttt gtg gct     1402
Glu Ser Gln Asp Lys Asn Leu Gly Glu Leu Ile Asp Arg Phe Val Ala
    435                 440                 445 gat ttc aaa gcc cag ggg cca cct aag ccc aac act gat gaa ggg ggt     1450
Asp Phe Lys Ala Gln Gly Pro Pro Lys Pro Asn Thr Asp Glu Gly Gly
450                 455                 460                 465 acc gtg ctc ccc agc tgc gcc gac ctc ttt gtc tac tac aag aag tgc     1498
Thr Val Leu Pro Ser Cys Ala Asp Leu Phe Val Tyr Tyr Lys Lys Cys
                470                 475                 480 atg gtg caa tgc tct cag ctc agt act ggg gag ccc atg atc gcc ctg     1546
Met Val Gln Cys Ser Gln Leu Ser Thr Gly Glu Pro Met Ile Ala Leu
            485                 490                 495 acc acc att ttc cag aag tac ctc cga gaa tac gcc tgg aaa atc ctc     1594
Thr Thr Ile Phe Gln Lys Tyr Leu Arg Glu Tyr Ala Trp Lys Ile Leu
        500                 505                 510 tct ggc aac ctg ccc aaa ccc aca acc agc agt gaa gga ctg act atc     1642
Ser Gly Asn Leu Pro Lys Pro Thr Thr Ser Ser Glu Gly Leu Thr Ile
    515                 520                 525 agc agc ctc ctc aag gaa aag gag ggc tca gaa gta gcc aag ttc act     1690
Ser Ser Leu Leu Lys Glu Lys Glu Gly Ser Glu Val Ala Lys Phe Thr
530                 535                 540                 545 ctg gag gag ctc tgc ctc atc tgt aac atc ctg agc acg gca gag tac     1738
Leu Glu Glu Leu Cys Leu Ile Cys Asn Ile Leu Ser Thr Ala Glu Tyr
                550                 555                 560 tgt ctg gcc acc acc cag cag cta gaa gaa aaa ctc aaa gaa aaa gtg     1786
Cys Leu Ala Thr Thr Gln Gln Leu Glu Glu Lys Leu Lys Glu Lys Val
            565                 570                 575 gat gta agt ctg att gaa cga atc aat ctg act gga gag atg gac acg     1834
Asp Val Ser Leu Ile Glu Arg Ile Asn Leu Thr Gly Glu Met Asp Thr
        580                 585                 590
```

-continued

| | | | | | | | | | | | | |
|---|---|---|---|---|---|---|---|---|---|---|---|---|
| ttc | agc | acc | gtc | atc | tcc | agc | agt | att | cag | ctg | ctg | gtt | cag | gat | ctg | 1882 |
| Phe | Ser | Thr | Val | Ile | Ser | Ser | Ile | Gln | Leu | Leu | Val | Gln | Asp | Leu |
| 595 | | | | 600 | | | | | 605 | | | | |

```
ttc agc acc gtc atc tcc agc agt att cag ctg ctg gtt cag gat ctg      1882
Phe Ser Thr Val Ile Ser Ser Ile Gln Leu Leu Val Gln Asp Leu
595                 600                 605 gat gct gcc tgt gat cct gcc ctg act gcc atg agc aag atg cag tgg      1930
Asp Ala Ala Cys Asp Pro Ala Leu Thr Ala Met Ser Lys Met Gln Trp
610             615                 620                 625 cag aac gtg gag cac gtt ggt gac cag agc ccc tac gtc acc tct gtc      1978
Gln Asn Val Glu His Val Gly Asp Gln Ser Pro Tyr Val Thr Ser Val
                630                 635                 640 att ctg cac atc aag cag aac gtc ccc atc atc cgt gac aac ccc gtg      2026
Ile Leu His Ile Lys Gln Asn Val Pro Ile Ile Arg Asp Asn Pro Val
            645                 650                 655 gct tcc aca cgc aag tac ttc act cag tta tgc gtt aaa ttt gca aag      2074
Ala Ser Thr Arg Lys Tyr Phe Thr Gln Leu Cys Val Lys Phe Ala Lys
        660                 665                 670 taa a                                                                 2078
```

<210> SEQ ID NO 2
<211> LENGTH: 673
<212> TYPE: PRT
<213> ORGANISM: Homo sapiens

<400> SEQUENCE: 2

```
Met Met Glu Glu Glu Glu Leu Glu Phe Val Glu Glu Leu Glu Ala Val
1               5                   10                  15

Leu Gln Leu Thr Pro Glu Val Gln Leu Ala Ile Glu Gln Val Phe Pro
            20                  25                  30

Ser Gln Asp Pro Leu Asp Arg Ala Asp Phe Asn Ala Val Glu Tyr Ile
        35                  40                  45

Asn Thr Leu Phe Pro Thr Glu Gln Ser Leu Ala Asn Ile Asp Glu Val
    50                  55                  60

Val Asn Lys Ile Arg Leu Lys Ile Arg Arg Leu Asp Asp Asn Ile Arg
65                  70                  75                  80

Thr Val Val Arg Gly Gln Thr Asn Val Gly Gln Asp Gly Arg Gln Ala
                85                  90                  95

Leu Glu Glu Ala Gln Lys Ala Ile Gln Gln Leu Phe Gly Lys Ile Lys
            100                 105                 110

Asp Ile Lys Asp Lys Ala Glu Lys Ser Glu Gln Met Val Lys Glu Ile
        115                 120                 125

Thr Arg Asp Ile Lys Gln Leu Asp His Ala Lys Arg His Leu Thr Thr
    130                 135                 140

Ser Ile Thr Thr Leu Asn His Leu His Met Leu Ala Gly Gly Val Asp
145                 150                 155                 160

Ser Leu Glu Ala Met Thr Arg Arg Gln Tyr Gly Glu Val Ala Asn
                165                 170                 175

Leu Leu Gln Gly Val Met Asn Val Leu Glu His Phe His Lys Tyr Met
            180                 185                 190

Gly Ile Pro Gln Ile Arg Gln Leu Ser Glu Arg Val Lys Ala Ala Gln
        195                 200                 205

Thr Glu Leu Gly Gln Gln Ile Leu Ala Asp Phe Glu Glu Ala Phe Pro
    210                 215                 220

Ser Gln Gly Thr Lys Arg Pro Gly Gly Pro Ser Asn Val Leu Arg Asp
225                 230                 235                 240

Ala Cys Leu Val Ala Asn Ile Leu Asp Pro Arg Ile Lys Gln Glu Ile
                245                 250                 255
```

```
Ile Lys Lys Phe Ile Lys Gln His Leu Ser Glu Tyr Leu Val Leu Phe
            260                 265                 270

Gln Glu Asn Gln Asp Val Ala Trp Leu Asp Lys Ile Asp Arg Arg Tyr
            275                 280                 285

Ala Trp Ile Lys Arg Gln Leu Val Asp Tyr Glu Lys Tyr Gly Arg
290                 295                 300

Met Phe Pro Arg Glu Trp Cys Met Ala Glu Arg Ile Ala Val Glu Phe
305                 310                 315                 320

Cys His Val Thr Arg Ala Glu Leu Ala Lys Ile Met Arg Thr Arg Ala
                325                 330                 335

Lys Glu Ile Glu Val Lys Leu Leu Phe Ala Ile Gln Arg Thr Thr
            340                 345                 350

Asn Phe Glu Gly Phe Leu Ala Lys Arg Phe Ser Gly Cys Thr Leu Thr
            355                 360                 365

Asp Gly Thr Leu Lys Lys Leu Glu Ser Pro Pro Ser Thr Asn Pro
370                 375                 380

Phe Leu Glu Asp Glu Pro Thr Pro Glu Met Glu Leu Ala Thr Glu
385                 390                 395                 400

Lys Gly Asp Leu Asp Gln Pro Lys Lys Pro Lys Ala Pro Asp Asn Pro
                405                 410                 415

Phe His Gly Ile Val Ser Lys Cys Phe Glu Pro His Leu Tyr Val Tyr
            420                 425                 430

Ile Glu Ser Gln Asp Lys Asn Leu Gly Glu Leu Ile Asp Arg Phe Val
            435                 440                 445

Ala Asp Phe Lys Ala Gln Gly Pro Pro Lys Pro Asn Thr Asp Glu Gly
450                 455                 460

Gly Thr Val Leu Pro Ser Cys Ala Asp Leu Phe Val Tyr Tyr Lys Lys
465                 470                 475                 480

Cys Met Val Gln Cys Ser Gln Leu Ser Thr Gly Glu Pro Met Ile Ala
                485                 490                 495

Leu Thr Thr Ile Phe Gln Lys Tyr Leu Arg Glu Tyr Ala Trp Lys Ile
            500                 505                 510

Leu Ser Gly Asn Leu Pro Lys Pro Thr Thr Ser Ser Glu Gly Leu Thr
            515                 520                 525

Ile Ser Ser Leu Leu Lys Glu Lys Glu Gly Ser Glu Val Ala Lys Phe
530                 535                 540

Thr Leu Glu Glu Leu Cys Leu Ile Cys Asn Ile Leu Ser Thr Ala Glu
545                 550                 555                 560

Tyr Cys Leu Ala Thr Thr Gln Gln Leu Glu Glu Lys Leu Lys Glu Lys
                565                 570                 575

Val Asp Val Ser Leu Ile Glu Arg Ile Asn Leu Thr Gly Glu Met Asp
            580                 585                 590

Thr Phe Ser Thr Val Ile Ser Ser Ile Gln Leu Leu Val Gln Asp
            595                 600                 605

Leu Asp Ala Ala Cys Asp Pro Ala Leu Thr Ala Met Ser Lys Met Gln
610                 615                 620

Trp Gln Asn Val Glu His Val Gly Asp Gln Ser Pro Tyr Val Thr Ser
625                 630                 635                 640

Val Ile Leu His Ile Lys Gln Asn Val Pro Ile Ile Arg Asp Asn Pro
                645                 650                 655

Val Ala Ser Thr Arg Lys Tyr Phe Thr Gln Leu Cys Val Lys Phe Ala
            660                 665                 670

Lys
```

```
<210> SEQ ID NO 3
<211> LENGTH: 17
<212> TYPE: DNA
<213> ORGANISM: Synthetic primer

<400> SEQUENCE: 3
gcagtgggcc atcatca                                                  17

<210> SEQ ID NO 4
<211> LENGTH: 17
<212> TYPE: DNA
<213> ORGANISM: Synthetic primer

<400> SEQUENCE: 4
ccgcagaagg ctgttgt                                                  17

<210> SEQ ID NO 5
<211> LENGTH: 18
<212> TYPE: DNA
<213> ORGANISM: Synthetic primer

<400> SEQUENCE: 5
atgatggagg aggaggaa                                                 18

<210> SEQ ID NO 6
<211> LENGTH: 18
<212> TYPE: DNA
<213> ORGANISM: Synthetic primer

<400> SEQUENCE: 6
gttgtcacgg atgatggg                                                 18

<210> SEQ ID NO 7
<211> LENGTH: 17
<212> TYPE: DNA
<213> ORGANISM: Synthetic primer

<400> SEQUENCE: 7
cgggtggcgg aatgatg                                                  17

<210> SEQ ID NO 8
<211> LENGTH: 18
<212> TYPE: DNA
<213> ORGANISM: Synthetic primer

<400> SEQUENCE: 8
ctccaccccc atctacca                                                 18

<210> SEQ ID NO 9
<211> LENGTH: 17
<212> TYPE: DNA
<213> ORGANISM: Synthetic primer

<400> SEQUENCE: 9
ggtggcggaa tgatgga                                                  17

<210> SEQ ID NO 10
<211> LENGTH: 17
<212> TYPE: DNA
<213> ORGANISM: Synthetic primer

<400> SEQUENCE: 10
caaaacgctt ctccggc                                                  17
```

```
<210> SEQ ID NO 11
<211> LENGTH: 19
<212> TYPE: DNA
<213> ORGANISM: Synthetic primer

<400> SEQUENCE: 11
tgcatggctg agaggattg                                          19

<210> SEQ ID NO 12
<211> LENGTH: 17
<212> TYPE: DNA
<213> ORGANISM: Synthetic primer

<400> SEQUENCE: 12
acaaccccgt ggcttcc                                            17

<210> SEQ ID NO 13
<211> LENGTH: 18
<212> TYPE: DNA
<213> ORGANISM: Synthetic primer

<400> SEQUENCE: 13
tgcgtaccag agcgaagg                                           18

<210> SEQ ID NO 14
<211> LENGTH: 18
<212> TYPE: DNA
<213> ORGANISM: Synthetic primer

<400> SEQUENCE: 14
caagcagaac gtccccat                                           18

<210> SEQ ID NO 15
<211> LENGTH: 17
<212> TYPE: DNA
<213> ORGANISM: Synthetic primer

<400> SEQUENCE: 15
aggatggacg gcaagcg                                            17

<210> SEQ ID NO 16
<211> LENGTH: 18
<212> TYPE: DNA
<213> ORGANISM: Synthetic primer

<400> SEQUENCE: 16
ggaggaccca gcaatgtt                                           18

<210> SEQ ID NO 17
<211> LENGTH: 19
<212> TYPE: DNA
<213> ORGANISM: Synthetic primer

<400> SEQUENCE: 17
ccaagacaag aacctcgga                                          19

<210> SEQ ID NO 18
<211> LENGTH: 18
<212> TYPE: DNA
<213> ORGANISM: Synthetic primer

<400> SEQUENCE: 18
aacatcctga gcacggca                                           18
```

HUMAN HEPATOMA ASSOCIATED PROTEIN AND THE POLYNUCLEOTIDE ENCODING SAID POLYPEPTIDE

FIELD OF INVENTION

This invention relates to the field of biotechnology, and, in particular, relates to the a novel polynucleotide encoding human hepatoma associated protein and the polypeptide encoded by said polynucleotide. The invention also relates to the uses and preparation of these polynucleotides and polypeptides. The hepatoma associated protein of the invention is a suppresser of hepatocellular carcinoma.

PRIOR ART

The mortality rate of malignant tumor is just lower than that of cardio- and cerebrovascular disease. Hepatocarcinoma is one of the most common tumors in China. The development of hepatocarcinoma is a complex process involving multiple genes and steps and effected by the activation of many oncogenes and inactivation of anti-oncogenes. The anti-oncogenes are much important. Therefore, to find anti-oncogenes are one of the focuses of the current studies. A high frequency of loss of heterozygosity (LOH) on a segment of chromosomes in a certain cancer suggests that there is an anti-oncogene associated with said cancer in this segment.

There is a high frequency of loss of heterozygosity on chromosome 17p13.3 in several tumors. Therefore, several laboratories in the world have tried to find out the anti-oncogenes in chromosome 17p13.3. Up to now, three possible anti-oncogene (Hic-I, OVCA1 and OVCA2) have been found. Hic-I is highly methylated and lowly expressed in tumor tissues. OVCA1 and OVCA2 are lowly expressed or not expressed at all in oophoroma tissue or cell lines. These three genes are all located near site YNZ22 of the chromosome.

Since cancer is one of the main diseases harmful to human health, people are concerned about the early diagnosis and gene therapy of cancer so as to effectively cure and prevent tumors, such as hepatocarcinoma. Therefore, there is a keen need in the art to develop new tumor-associated and/or tumor-inhibiting human proteins and their agonist/antagonist.

SUMMARY OF INVENTION

One purpose of the invention is to provide a novel hepatoma associated protein, which is named c63R protein, and its fragments, analogs and derivatives.

Another purpose of the invention is to provide a polynucleotide encoding said polypeptides.

Still another purpose of the invention is to provide a method for preparing said polypeptides and the uses of said polypeptides and their encoding sequences.

In the first aspect, the invention provides an isolated human c63R polypeptide, which comprises a polypeptide having the amino acid sequence of SEQ ID NO: 2, its conservative variants, its active fragments, and its active derivatives. Preferably, said polypeptide is a polypeptide having the amino acid sequence of SEQ ID NO: 2.

In the second aspect, the invention provides an isolated polynucleotide, which comprises a nucleotide sequence sharing at least 85% homology to the following nucleotide sequence: (a) the nucleotide sequence encoding the above c63R polypeptide; (b) the polynucleotide complementary to nucleotide sequence of (a). Preferably, said nucleotide sequence encodes a polypeptide comprising the amino acid sequence of SEQ ID NO: 2. More preferably, said polynucleotide comprises the ORF sequence or full-length sequence of SEQ ID NO: 1.

In the third aspect, the invention provides a vector comprising the above polynucleotide and a host cell transformed with said vector, a host cell transformed with said polynucleotide.

In the fourth aspect, the invention provides a method for producing a polypeptide having the activity of c63R protein, which comprises:

(a) culturing the above transformed host cell under the conditions suitable for the expression of protein;

(b) isolating the polypeptides having the activity of c63R protein from the culture.

In the fifth aspect, the invention provides an antibody specifically bound to c63R protein. Also provided are nucleic acid molecules comprising consecutive 10–800 nucleotides of the above polynucleotide.

In the sixth aspect, the invention provides pharmaceutical composition comprising a safe and efficient amount of hepatocarcinoma associated c63R protein and pharmaceutically acceptable carrier. Said pharmaceutical composition can be used for the therapy of diseases, such as cancer and cell abnormal proliferation.

In the seventh aspect, the invention provides a method for detecting the carcinomatous change or cancer susceptibility of hepatocytes, comprising the steps of: detecting whether there is any change of c63R transcript in the hepatocyte sample when compared with the normal c63R transcript, and said change indicating that the hepatocyte has developed cancer or is cancer susceptible; or detecting whether there is any change of activity of c63R protein in the hepatocyte sample when compared with the normal c63R protein, and said change indicating that the hepatocyte has developed cancer or is cancer susceptible. Preferably, said change is nucleotide deletion, insertion or substitution. More preferably, said change is selected from the group consisting of: deletion of nucleotides 395–481 in SEQ ID NO: 1, deletion of nucleotides 328–1511 in SEQ ID NO: 1, deletion of nucleotides 1143–1231 in SEQ ID NO: 1, deletion of nucleotides 1325–1419 in SEQ ID NO: 1, change from C to T of nucleotide 1106 in SEQ ID NO: 1, deletion of nucleotide 1048 in SEQ ID NO: 1.

In the eighth aspect, the invention provides a kit for detecting hepatocarcinoma comprising: (1) a pair of primers specifically amplifying human c63R gene, (2) the agents for detecting whether there is any change between the amplification product and the normal c63R gene.

The other aspects of the invention will be apparent to the skilled in the art in light of the technical disclosure of the invention.

FIG. 1 shows the contig of genomic clones covering HCCS1 and the gene structure of HCCS1.

Markers used in genomic clone screening and contig construction are shown at the top.

The contig of genomic clones covering HCCS1 is shown in the middle. The exons of HCCS1 are shown at the bottom.

Figures 2A, 2B, 2C:
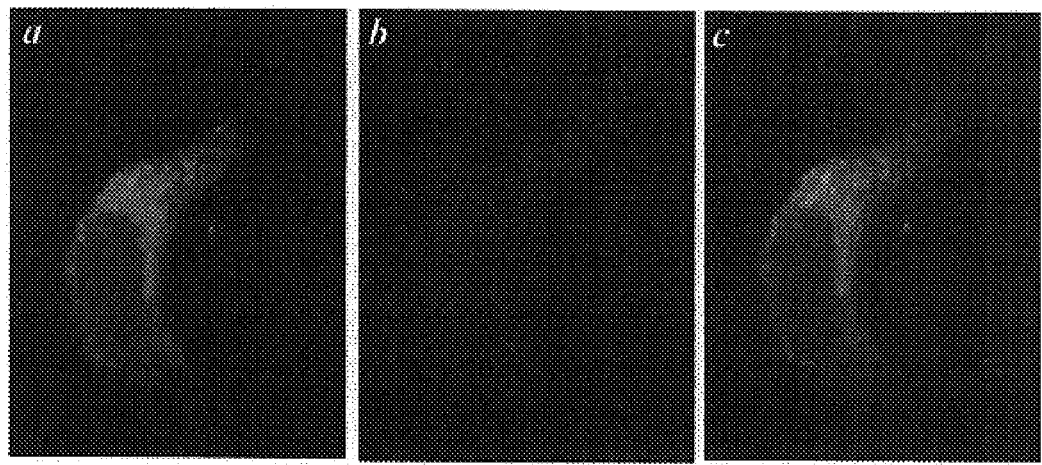

FIG. 2 shows the locations of HCCS1 in cells. FIG. 2A is a fluorescence photo of NIH/3T3 cells transfected with pEGFP-HCCS1. FIG. 2B is an immunofluorescence photo stained with anti-mitochondria antibody of cells shown in FIG. 2a. FIG. 2c is the overlay image of FIGS. 2a and 2b, indicating the localization of HCCS1 is at mitochondria.

Figure 3:
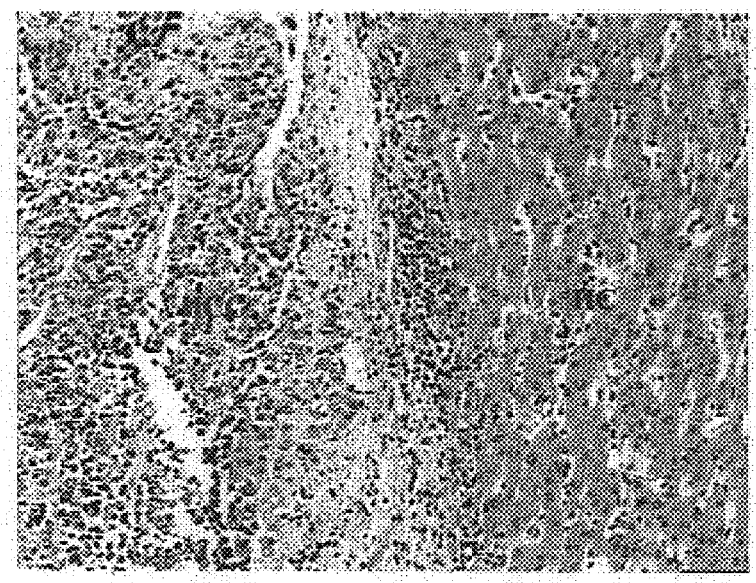

FIG. 3 shows the immunohistochemical staining of human HCC and surrounding noncancerous tissues. HCC: hepatocarcinoma cell. HC, hepatocytes.

Figures 4A, 4B:
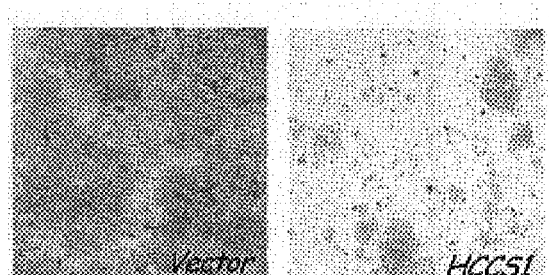
Figure 4C:
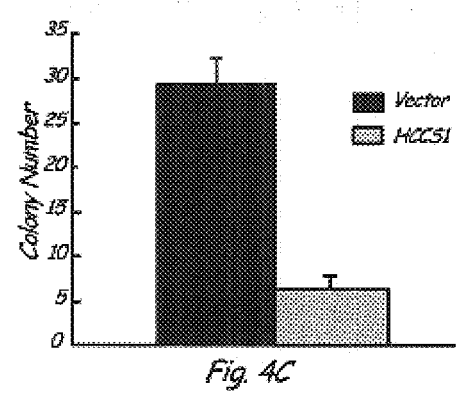

FIG. 4 shows the effect of HCCS1 expression on cell growth. FIG. 4A, colony formation of SMMC-7721 cells transfected with vector pcDNA3.1/V5-His. FIG. 4B, colony formation of SMMC-7721 cells transfected with vector containing HCCS1 cDNA. FIG. 4C, diagram of colony formation assay in triplicate. P<0.01 in comparison with the vector group.

Figure 5:
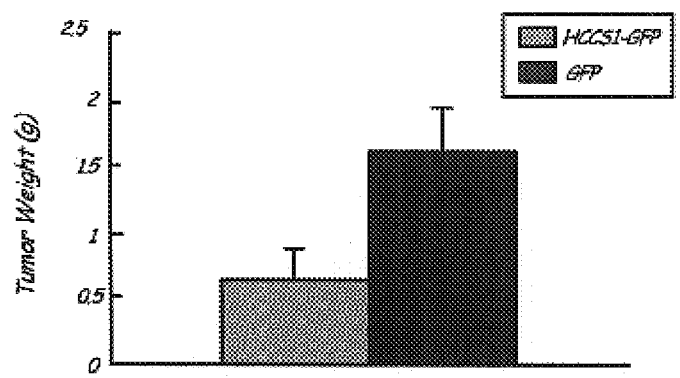

FIG. 5 shows the effect of HCCS1 on the tumor formation in nude mice. P<0.01 in comparison with GFP vector control group.

DETAILED DESCRIPTION OF INVENTION

In the hepatocarcinoma study, the inventors have found that the region of LOH in chromosomes 17p13.3 is located from YNZ22 site to D17S34 of telomere. The minimum region of LOH is within the region between D17S643 and D17S1574. The inventors have cloned the genes in this region and obtained c63R gene in D17S849. It has been found there are deletion and frameshift mutation of c63R gene in HCC tissue, confirming c63R gene is a HCC associated gene. Further experiments demonstrated that c63R gene is a hepatocellular carcinoma suppressor so that c63R is also referred to as HCCS1 (Hepatoceullular Carcinoma Suppresser 1). It has been indicated in the studies that HCCS1 is located in mitochondria. Moroever, HCCS1 is negatively expressed in hepatocarcinoma cells and positively expressed in normal hepatocyte. After transformed into HCC cell and nude mice, HCCS1 inhibits the growth of tumor cell and formation of tumor.

As used herein, the terms "c63R protein", "c63R polypeptide", "HCC associated protein c63R", "HCCS1 protein", "HCCS1 polypeptide", and "Hepatocellular Carcinoma suppresser HCCS1" are changeable. Each of them means a protein or polypeptide having the amino acid sequence of human HCC associated protein c63R (SEQ ID NO: 2). These terms also include the HCC associated protein c63R having or not having the starting Met residue.

As used herein, the term "isolated" refers to a substance which has been isolated from the original environment. For naturally occurring substance, the original environment is the natural environment. For example, the polynucleotide and polypeptide in a naturally occurring state in the viable cells are not isolated or purified. However, if the same polynucleotide and polypeptide have been isolated from other components naturally accompanying them, they are isolated or purified.

As used herein, the terms "isolated HCC associated c63R protein or polypeptide" or "isolated c63R protein or polypeptide" means that human c63R protein does not essentially contain other proteins, lipids, carbohydrate or any other substances associated therewith in nature. The skilled in the art can purify human c63R protein by standard protein purification techniques. Essentially purified polypeptide forms a single main band on a non-reductive PAGE gel. The purity of human c63R protein polypeptide can be analyzed by amino acid sequence analysis.

The polypeptide of invention may be a recombinant polypeptide, natural polypeptide, or synthetic polypeptide, preferably a recombinant polypeptide. The polypeptide of invention may be a purified natural product or a chemically synthetic product. Alternatively, it may be produced from prokaryotic or eukaryotic hosts, such as bacteria, yeast, higher plant, insect, and mammal cells, using recombinant techniques. According to the host used in the protocol of recombinant production, the polypeptide of invention may be glycosylated or non-glycosylated. The polypeptide of invention may or may not comprise the starting Met residue.

The invention further comprises the fragments, derivatives and analogues of human c63R protein. As used in the invention, the terms "fragment", "derivative" and "analogue" mean the polypeptide that essentially retains the same biological functions or activity of HCC associated human c63R protein of the invention. The fragment, derivative or analogue of the polypeptide of invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues include a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretary sequence or a sequence which is employed for purification of the mature polypeptide or a proportion sequence. Such fragments, derivatives and analogs are deemed to be within the scope of those skilled in the art from the teachings herein.

The polynucleotide according to the invention may be in the forms of DNA and RNA. DNA includes cDNA, genomic DNA, and synthetic DNA, etc., in single strand or double strand form. A single strand DNA may be an encoding strand or non-encoding strand. The coding sequence for mature polypeptide may be identical to the coding sequence shown in SEQ ID NO: 1, or is a degenerate sequence. As used herein, the term "degenerate sequence" means an sequence which encodes a protein or peptide comprising a sequence of SEQ ID NO: 2 and which has a nucleotide sequence different from the sequence of coding region in SEQ ID NO: 1.

The sequences encoding the mature polypeptide include those encoding only the mature polypeptide, those encoding mature polypeptide plus various additional encoding sequence, the encoding sequence for mature polypeptide plus the non-encoding sequence and optional additional encoding sequence.

The term "polynucleotide encoding the polypeptide" includes the polynucleotide encoding said polypeptide and the polynucleotide comprising additional and/or non-encoding sequence.

The invention further relates to the variants of the hereinabove polynucleotides which encode a polypeptide having the same amino acid sequence of invention, or its fragment, analogue and derivative. The variant of the polynucleotide may be a naturally occurring allelic variant of the polynucleotide or a non-naturally occurring variant of the polynucleotide. Such nucleotide variants include substitution, deletion, and insertion variants. As known in the art, the allelic variant is a substitution form of polynucleotide, which may be a substitution, deletion, and insertion of one or more nucleotides without substantially changing the functions of the encoded polypeptide.

The present invention further relates to polynucleotides, which hybridize to the hereinabove-described sequences, if there is at least 50% and preferably at least 70% identity between the sequences. The present invention particularly relates to polynucleotides, which hybridize under stringent conditions to the polynucleotides of the invention. As herein used, the term "stringent conditions" means the following conditions: (1) hybridization and washing under low ionic strength and high temperature, such as 0.2×SSC, 0.1% SDS, 60° C.; (2) hybridization after adding denaturants, such as 50% (v/v) formamide, 0.1% bovine serum/0.1% Ficoll™, 42° C.; or (3) hybridization of two sequences sharing at least 95%, preferably 97% homology. Further, the polynucleotides which hybridize to the hereinabove described polynucleotides encode a polypeptide which retains the same biological function or activity as the mature polypeptide as set forth in SEQ ID NO: 2.

The invention also relates to nucleic acid fragments hybridized with the hereinabove sequence. As used in the present invention, the length of the "nucleic acid fragment" is at least 15 bp, preferably at least 30 bp, more preferably at least 50 bp, and most preferably at least 100 bp. The nucleic acid fragment can be used in the amplification techniques of nucleic acid, e.g., PCR, so as to determine and/or isolate the polynucleotide encoding c63R protein.

The polypeptide and polynucleotide of the invention are preferably in isolated form, preferably purified to be homogenous.

According to the invention, the DNA sequence encoding can be obtained in various ways. For example, the polynucleotide is isolated by the hybridization techniques well-known in the art, which includes, but are not limited to 1) the hybridization between the probe and genomic or cDNA library so as to select the homologous polynucleotide sequence, and 2) expression of the antibodies against the library so as to screen out the DNA fragments having the common structure features.

The specific DNA fragment sequences encoding c63R protein may further be obtained by the following methods so as to obtain the double-stranded DNA for said polypeptide: 1) isolating double-stranded DNA sequence from genomic DNA; and 2) chemical synthesis of DNA sequence.

In the above methods, the isolation of genomic DNA is least frequently used. The direct channel synthesis of DNA sequence is commonly used when the whole amino acid sequence of the desired polypeptide product is known. When the whole amino acid sequence of the desired polypeptide product is not known, the direct chemical synthesis of DAN sequence is impossible and the method is to isolate cDNA sequence. The standard method for isolating the cDNA of interest is to isolate mRNA from donor cells that highly express said gene followed by reverse transcription of mRNA to form plasmid or phage cDNA library. These are many sophisticated techniques for extracting mRNA and the kits are commercially available (Qiagen). The conventional method can be used to construct cDNA library (Sambrook, et al., Molecular Cloning, A Laboratory Manual, Cold Spring Harbor Laboratory. New York, 1989). The cDNA libraries are also commercially available, e.g., the different cDNA library from Clontech. When PCR is used in combination, even an extremely small amount of expression products can be cloned.

The conventional methods can be used for screening the gene of invention from a library. These methods include, but are not limited to, (1) DNA-DNA or DNA-RNA hybridization, (2) the appearance or loss of the function of marker gene, (3) the determination of the level of c63R transcripts, (4) the determination of protein product of gene by immunology methods or the biological activity assays. These methods can be used alone or in combination.

In method (1), the probe used in the hybridization could be identical to any portion of polynucleotide of invention. The length of probe is typically at least 15, preferably at least 30, more preferably at least 50, and most preferably at least about 100 nucleotides. Usually, the length of probe is less than 2 kb, preferably 1 kb. The probe usually is the DNA sequence chemically synthesized on the basis of the sequence information of gene of invention. Of course, the gene of invention itself or the fragment thereof can be used as a probe. The labels for DNA probe include, e.g., radioactive isotopes, fluoresceins or enzymes, such as alkaline phosphatase.

In method (4), the detection of the protein products expressed by c63R gene can be carried out by immunology methods, such as Western blotting, radioimmunoassay, and ELISA.

The method of amplification of DNA/RNA by PCR (Saiki, et al. Science 1985; 230:1350–1354) is preferably used to obtain the gene of the invention. Especially when it is difficult to obtain the full-length cDNA, the method of RACE is preferably used. The primers used in PCR can be properly selected according to the polynucleotide sequence information of invention disclosed herein and synthesized by the conventional methods. The amplified DNA/RNA fragments can be isolated and purified by conventional methods such as gel electrophoresis.

For the gene of the invention or its DNA fragments, the sequencing of polynucleotide sequence can be carried out by the conventional dideoxy sequencing method (Sanger et al. PNAS, 1977, 74: 5463–5467). The sequencing of polynucleotide sequence can also be carried out using the commercially available sequencing kits. In order to obtain the full-length cDNA sequence, it is necessary to repeat the sequencing. Sometimes, it may sequence the DNA of several clones to obtain the full-length cDNA sequence.

The invention further relates to a vector comprising the polynucleotide of the invention, a genetic engineered host cell transformed with the vector of the invention or directly with the sequence encoding c63R protein, and the method for producing the polypeptide of invention by recombinant techniques.

The recombinant c63R polypeptides can be expressed or produced by the conventional recombinant DNA technology (Science, 1984; 224:1431), using the polynucleotide sequence of invention. Generally, it comprises the following steps:

(1) transfecting or transforming the appropriate host cells with the polynucleotide encoding c63R polypeptide of the invention or the vector containing said polynucleotide;

(2) culturing the host cells in an appropriate medium;

(3) isolating or purifying the protein from the medium or cells.

In the present invention, the polynucleotide sequences encoding human c63R protein may be inserted into a recombinant expression vector. The term "expression vector" refers to a bacterial plasmid, bacteriophage, yeast plasmid, plant virus or mammal cell virus, such as adenovirus, retrovirus, or any other vehicles known in the art. Vectors suitable for use in the present invention include, but are not limited to, the T7-based expression vector for expression in bacteria (Rosenberg, et al., Gene, 56:125, 1987), the pMSXND expression vector for expression in mammalian cells (Lee and Nathans, J. Biol. Chem., 263:3251, 1988) and baculovirus-derived vectors for expression in insect cells. On the whole, any plasmid or vector can be used to construct the recombinant expression vector as long as it can replicate and is stable in the host. One important feature of expression vector is that the expression vector typically contains an origin of replication, a promoter, a marker gene as well as the translation regulatory components.

The methods known by the artisans in the art can be used to construct an expression vector containing the DNA sequence of c63R and appropriate transcription/translation regulatory components. These methods include in vivo recombinant DNA technique, DNA synthesis technique, in vivo recombinant technique and so on (Sambrook, et al. Molecular Cloning, a Laboratory Manual, Cold Spring Harbor Laboratory. New York, 1989). The DNA sequence is efficiently linked to the proper promoter in an expression vector to direct the synthesis of mRNA. The exemplary promoters are lac or trp promoter of E.coli; $P_L$ promoter of λ phage; eukaryotic promoter including CMV immediate early promoter, HSV thymidine kinase promoter, early and late SV40 promoter, LTRs of retrovirus and some other known promoters which control the gene expression in the prokaryotic cells, eukaryotic cells or virus. The expression vector may further comprise a ribosome binding site for initiating the translation, transcription terminator and the like.

Further, the expression vector preferably comprises one or more selective marker genes to provide a phenotype for the selection of the transformed host cells, e.g., the dehydrofolate reductase, neomycin resistance gene and GFP (green fluorescent protein) for eukaryotic cells, as well as tetracycline or ampicillin resistance gene for E. coli.

The vector containing said DNA sequence and proper promoter or regulatory elements can be transformed into appropriate host cells to express the protein.

The "host cell" includes prokaryote, such as bacteria; primary eukaryote, such as yeast; advanced eukaryotic, such as mammalian cells. The representative examples are bacterial cells, such as E. coli, Streptomyces, Salmonella thyphimurium; fungal cells, such as yeast; plant cells; insect cells such as Drosophila S2 or Sf9; animal cells such as CHO, COS or owes melanoma, etc.

Transcription of the polynucleotide of invention in higher eukaryotes is increased by inserting an enhancer sequence into the vector. Enhancers are cis-acting elements of DNA, usually about from 10 to 300 bp that act on a promoter to increase the gene transcription. Examples include the SV40 enhancer on the late side of the replication origin 100 to 270 bp, the polyoma enhancer on the late side of the replication origin, and adenovirus enhancers.

The skilled in the art know clearly how to select appropriate vectors, promoters, enhancers and host cells.

Recombinant transformation of host cell with the DNA sequence of invention might be carried out by conventional techniques well known to those skilled in the art. Where the host is prokaryotic such as E. coli, the competent cells, which are capable of DNA uptake, can be prepared from cells harvested after exponential growth phase and subsequently treated by the $CaCl_2$ method using procedures well known in the art. Alternatively, $MgCl_2$ can be used. The transformation can also be carried out by electroporation, if desired. When the host is an eukaryote, such methods of transfection of DNA as calcium phosphate co-precipitates, conventional mechanical procedures such as micro-injection, electroporation, or liposome-mediated transfection may be used.

The transformants are cultured using conventional methods to express the polypeptides of the invention. According to the used host cells, the medium for cultivation can be selected from various conventional mediums. The host cells are cultured under a condition suitable for its growth until the host cells grow to an appropriate cell density. Then, the selected promoter is induced by appropriate means (e.g., temperature shift or chemical induction) and cells are cultured for an additional period.

In the above methods, the recombinant polypeptide may be included in the cells, or expressed on the cell membrane, or secreted out of the cell. If desired, the physical, chemical and other properties can be utilized in various isolation methods to isolate and purify the recombinant protein. These methods are well-known to those skilled in the art and include, but are not limited to conventional renaturation treatment, treatment by protein precipitant (such as salt precipitation), centrifugation, cell lysis by osmosis, sonication, supercentrifugation, molecular sieve chromatography or gel chromatography, adsorption chromatography, ion exchange chromatography, HPLC, and any other liquid chromatography, and the combination thereof.

The studies of the invention showed that, in the cancerous cells, almost all of c63R genes existed mutations including deletions, insertions and substitution in the c63R encoding sequence and non-coding sequence. These mutations make c63R protein have no or low activity in hepatocyte, finally directly or indirectly causing HCC.

Therefore, the recombinant HCC associated c63R protein or polypeptide have various uses including, but not limited to: curing disorders (e.g., HCC) caused by low or no activity of c63R protein, and screening out antibodies, polypeptides or ligands as agonists or antagonists of c63R. For example, antibodies can be used to activate or inhibit the function of c63R protein. The expressed recombinant c63R protein can be used to screen polypeptide library to find out therapeutically valuable polypeptide molecules which inhibit or activate c63R protein.

The invention also provides the method for screening compounds so as to identify agents which improve c63R protein (agonists) or repress c63R protein (antagonists). For example, in the presence of an agent, the mammal cells or the membrane preparation expressing c63R protein can be incubated wit the labeled c63R protein to determine the ability of the agent to enhance or repress the interaction.

The antagonists of c63R protein include the screened antibodies, compounds, receptor deletants and analogues. The antagonists of c63R protein can bind to c63R protein and eliminate its function, or inhibit the production of c63R, or bind to the active site of said polypeptide so that the polypeptide can not function biologically.

When screening the compound as an antagonist, c63R protein may be added into the biological assay. One can determine whether the compound is an antagonist by determining the its effect on the interaction between c63R protein and its receptor. Using the method same as that for screening compounds, one can screen out the receptor deletants and analogues acting as antagonists.

The polypeptide of invention can be directly used for the treatment of diseases, e.g., various malignant tumors, abnormal cell proliferation, especially HCC.

The polypeptide, and its fragment, derivative, analogue or cells can be used as antigens to produce antibodies. These antibodies may be polyclonal or monoclonal antibodies. The polyclonal antibodies can be prepared by immunizing animals with c63R protein. The techniques for producing monoclonal antibodies against c63R protein include, but are not limited to, the hybridoma technique, the trioma technique, the human B-cell hybridoma technique, the EBV-hybridoma technique and so on.

According to the invention, the polypeptides, and its antagonists may be employed in combination with a suitable pharmaceutical carrier. Such a carrier includes but is not limited to water, glucose, ethanol, salt, buffer, glycerol, and combinations thereof. Such compositions comprise a safe and effective amount of the polypeptide or antagonists, as well as a pharmaceutically acceptable carrier or excipient which does not influence the effect of the drug. These compositions can be used for treatment of disease.

The invention also provides a pharmaceutical pack or kit comprising one or more containers filled with one or more of the ingredients of the pharmaceutical compositions of the invention. Associated with such container(s) can be a notice in the form prescribed by a government agency regulating the manufacture, use or sale of pharmaceuticals or biological products, which notice reflects approval by the agency of manufacture, use or sale for human administration. In addition, the polypeptides of the invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. The c63R protein is administered in an amount, which is effective for treating and/or prophylaxis of the specific indication. The amount of c63R protein administrated on patient will depend upon various factors, such as delivery methods, the subject health, and the like, and is within the judgment of the skilled clinician.

c63R polynucleotides also have many therapeutic applications. Gene therapy technology can be used in the therapy of the abnormal cell proliferation, development or metabolism, which is caused by the loss of c63R expression or the expression of abnormal or non-active c63R. Recombinant gene therapy vectors, such as virus vectors, can be designed to express mutated c63R so as to inhibit the activity of endogenous c63R. One form of the mutated c63R is a truncated c63R whose signal transduction domain is deleted. Therefore, this mutated c63R can bind the downstream substrate without the activity of signal transduction. Thus, the recombinant gene therapy vectors can be used to cure the disease caused by the abnormal expression or activity of c63R. The expression vectors derived from virus, such as retrovirus, adenovirus, adeno-associated virus, herpes simplex virus, parvovirus, and so on, can be used to introduce the c63R gene into the cells. The methods for constructing a recombinant virus vector harboring c63R gene are described in the literature (Sambrook, et al.). In addition, the recombinant c63R gene can be packed into liposome and then transferred into the cells.

Also included in the invention are ribozyme and the oligonucleotides, including antisense RNA and DNA, which inhibit the translation of c63R mRNA. Ribozyme is an enzyme-like molecule capable of specifically cutting certain RNA. The mechanism is the nucleic acid endo-cleavage after the specific hybridization of ribozyme molecule and the complementary target RNA. Antisense RNA and DNA as well as ribozyme can be prepared by using any conventional techniques for RNA and DNA synthesis, e.g., the widely used solid phase phosphite chemical method for oligonucleotide synthesis. Antisense RNA molecule can be obtained by the in vivo or in vitro transcription of the DNA sequence encoding said RNA, wherein said DNA sequence is integrated into the vector and in the downstream of RNA polymerase promoter. In order to increase stability, the nucleic acid molecules can be modified in many manners, e.g., increasing the length of the flanking sequences, replacing the phosphodiester bond with the phosphothioester bond in the oligonucleotide.

The methods for introducing the polynucleotides into tissues or cells include: directly injecting the polynucleotides into tissue in the body, in vitro introducing the polynucleotides into cells with vectors, such as virus, phage, or plasmid, and then transplanting the cells into the body.

The polypeptide of invention is useful in the analysis of peptide spectrum. For example, the polypeptide can be specifically cut by physical, chemical, or enzymatic means, and then analyzed by one, two or three dimensional gel electrophoresis.

The invention also provides the antibodies against the determinants of c63R protein. These antibodies include, but are not limited to, polyclonal antibody, monoclonal antibody, chimeric antibody, single-chain antibody. Fab fragment and the fragments produced by Fab expression library.

The antibody against c63R protein can be used in immunohistochemical method to detect the presence of c63R protein in the biopsy specimen.

The monoclonal antibody specific to c63R protein can be labeled by radioactive isotopes, and injected into human body to trace the location and distribution of c63R protein. This radioactively labeled antibody can be used in the non-wounding diagnostic method for the mapping of the tumor and determination of the metastasis of tumor cells.

The antibody of the invention is useful for the therapy or the prophylaxis of disorders related to the c64R protein. The appropriate amount of antibody can be administrated to stimulate or block the production or activity of c63R.

Antibodies can also be designed as an immunotoxin targeting at the particular site in the body. For example, a monoclonal antibody having high affinity to c63R protein can be covalently bound to bacterial or plant toxins, such as diphtheria toxin, ricin, ormosine. One common method is to challenge the amino group on the antibody with sulfydryl cross-linking agents, such as SPDP, and bind the toxin onto the antibody by interchanging the disulfide bonds. This hybrid antibody can be used to kill c63R protein-positive cells.

The polyclonal antibodies can be prepared by immunizing animals, such as rabbit, mouse, and rat, with c63R protein. Various adjuvants, e.g., Freund's adjuvant, can be used to enhance the immunization.

The techniques for producing c63R protein monoclonal antibodies include the hybridoma technique (Kohler and Milstein. Nature, 1975, 256:495–497). The chimeric antibody comprising a constant region of human origin and a variable region of non-human origin can be produced using the conventional method in the art (Morrison et al, PNAS, 1985,81:6851). Furthermore, the techniques for producing single-chain antibody (U.S. Pat. No. 4,946,778) are also useful for preparing the single-chain antibody agent c63R protein.

The polypeptide molecule capable of binding to c63R protein can be obtained by screening out the random polypeptide library consisting of the various combinations of amino acids bound onto the solid matrix. Typically, c63R protein is labeled in the screening.

The invention further provides diagnostic assays for quantitative and in situ measurement of c63R protein level. These assays are well known in the art and include FISH assay and radioimmunoassay. The level of c63R protein detected in the assay can be used to illustrate the importance of c63R protein in diseases and to determine the diseases associated with c63R protein.

The polynucleotide encoding c63R protein can be used in the diagnosis of c63R protein related diseases. The polynucleotide encoding c63R can be used to detect whether c63R is expressed or not, and whether the expression of c63R is normal or abnormal, e.g., in the case of diseases. c63R DNA sequences can be used in the hybridization with biopsy samples to determine the expression of c63R. The hybridization methods include Southern blotting, Northern blotting and in situ blotting, etc., which are public and sophisticated techniques. The corresponding kits are commercially available. A part of or all of the polynucleotides of the invention can be used as probe and fixed on a microarray or DNA chip for analysis the differential expression of genes in tissues and for the diagnosis of genes. The c63R specific primers can be used in RNA-polymerase chain reaction and in vitro amplification to detect the transcripts of c63R.

Further, detection of the mutation of c63R gene is useful for the diagnosis of c63R protein related diseases. The mutation forms of c63R include site mutations, translocation, deletion, rearrangement and any other mutations compared with the wild-type c63R DNA sequence (e.g., the normal sequence of SEQ ID NO: 1). The conventional methods, such as Southern blotting, DNAs sequencing, PCR and in situ blotting, can be used to detect mutation. Moreover, mutation sometimes affects the expression of protein. Therefore, Northern blotting and Western blotting can be used to indirectly determine whether the gene is mutated or not.

The full length c63R nucleotide sequence or its fragment of the invention can be prepared by PCR amplification, recombinant method and synthetic method. For PCR amplification, one can obtain said sequences by designing primers based on the nucleotide sequence disclosed in the invention, especially the sequence of ORF, and using cDNA library commercially available or prepared by routine techniques known in the art as a template. When the sequence is long, it is usually necessary to perform two or more PCR amplifications and link the amplified fragments together in the correct order.

Once the sequence is obtained, a great amount of the sequences can be produced by recombinant methods. Usually, said sequence is cloned in a vector which is then transformed into a host cell. Then the sequence is isolated from the amplified host cells using conventional techniques.

Further, the sequence can be produced by synthesis, especially when the fragment is short. Typically, several small fragments are synthesized and linked together to obtain a long sequence.

At present, it is completely feasible to chemically synthesize the DNA sequence encoding the protein of the invention, or the fragments or derivatives thereof. In addition, the mutation can be introduced into the sequence of the protein by chemical synthesis.

Since the c63R protein of invention has the nature amino acid sequence from human, it is predicted that, compared with the other proteins in the same family from other animals, it has higher activity and/or lower side-effect when administrated to human. For example, there is no or low immunogenicity in vivo.

The invention is further illustrated by the following examples. It is appreciated that these examples are only intended to illustrate the invention, but not to limit the scope of the invention. For the experimental methods in the following examples, they are performed under routine conditions, e.g., those described by Sambrook, et al., in Molecular Clone: A Laboratory Manual, New York: Cold Spring Harbor Laboratory Press, 1989, or as instructed by the manufacturers, unless otherwise specified.

EXAMPLE 1

Determination of LOH Region in Chromosome 17p13.3 in HCC

In this Example, the analysis of LOH in HCC tissue was carried out by using polymorphic markers in chromosome 17p13.3, so as to determine the LOH region and the minimum frequent LOH region.

1. HCC and noncancerous tissue samples:

The HCC and noncancerous tissue of 54 primary HCC cases were obtained from Qi Dong Liver Cancer Institute. The tissues were cut in the operation, immediately frozen, and stored at −80° C.

2. Extraction of tissue DNA

The tissues were taken out from the low-temperature refrigerator, placed in a mortar-grinder and milled. The extraction of tissue DNA were carried out according to SDS/proteinase K-phenol/chloroform extraction.

3. Analysis of LOH

LOH was detected by using VNTR (variable number of tandem repeat) and RFLP probes in the Southern blotting analysis. 10 μg HCC and noncancerous tissue DNA were digested with proper restriction enzymes, run electrophoresis at 25V for 13 hr, and transferred onto the Hybond™-N membrane (Amersham), YNZ22 probe was given as a gift by Huyin from Shanghai Medical University. Probes 144D6 and YNH37.3 were bought from American Type Culture Collection (ATCC). Probes cCI17-708 and cCI17-680 were given by Dr. Nakamura. The probes were labeled with ((−$^{32}$P (dATP in a random priming method. For these probes, the site names and the restriction enzymes were listed in Table 1. Probes YNZ22.1, 144D6 and YNH37.3 were incubated overnight at 42° C. in a conventional hybridization solution containing 50% formamide. For the hybridization of Probes cCI17-708 and cCI17-680, pre-hybridization solution was 50% formamide, 5×SSC, 0.5% SDS, 10×Denhardt's solution, 250 μg/ml human placent DNA and pre-hybridization was 42° C. for 24 hr. For hybridization solution, except for the replacement of 10×Denhardt's solution by 10% dextran, sulfate solution, the other components were identical to those of pre-hybridization solution. The hybridization was 42° C. overnight.

The analysis of microsatellite markers was in a 12.5 ul reaction volume containing 1 uM PCR primers, 25 ng tissue DNA, 200 uM dNTP, 50 mM KCl, 10 mM Tris (pH9.0), 1.5 mM MgCl$_2$, 0.625 U Taq DNA polymerase (Promega). The names of microsattellite markers and annealing temperatures were listed in Table 1. The protocol of PCR was 97° C. for 4 min; 94° C. for 1 min, annealing at proper temperature for 1 min, and 72° C. for 1 min, for 30 cycles; and extending at 72° C. for 10 min. The products were detected in 2% agarose gel electrophoresis. One primer was labeled with [r-$^{32}$P]ATP. In the 5 ul PCR reaction volume, the system contained 1 pmol labeled primer, 1 ul above PCR product, 0.25 U Taq DNA polymerase. Except that the PCR reaction was carried out 4 cycles, the other reaction conditions and components were the same as above. After denaturation, PCR products were isolated on a 6% denaturing polyacrylamide gel, and observed for LOH results.

The LOH for a total of 16 polymorphic markers was detected in chromosome 17p13.3. The LOH frequencies for these markers were listed in Table 1. For each sample, the LOH of each site were summarized in Table 2. First, 22 samples were detected for LOH at YNZ22 site and 12 or 19 heterozygotes had LOH with a frequency of 63%. Then, 21 samples were detected for LOH at D17S34 site near telomere and 8 of 12 heterozygotes had LOH with a frequency 67%. It was of great interest that all of LOH positive samples at YNZ22 site had LOH at D17S34 site except the homozygotes, suggesting in HCC samples, the LOH region in 17p13.3 was at least from YNZ22 site to D17S34 site which was near telomere. Based on this consideration, 14 markers around these two sites were selected for further detection of LOH in HCC samples. The results showed that the 8 markers between D17S34 and D17S5 had high LOH in HCC samples, and the 3 markers at D17S5 and proximal to centromere had low or no LOH. This confirmed our presumption that the loss region in chromosome 17p13.3 was from D17S34 to D17S5 site in HCC samples. 22 samples were detected using D17S926 marker. Each of 10 heterozygotes had LOH and the frequency was 100%. The samples having LOH at YNZ22 site also had LOH at this site except the hymozygotes. D17S1866, D17S849, D17S643, D17S1840, D17S654 and D17S1574 markers also were shown LOH in the samples having LOH at YNZ22 site, except the homozygotes and the frequency was 68–86%. Probe YNH37.3 (D17S28) was used to detect 9 samples having LOH at YNZ22 site. When cleavaged with Taq I, all these 9 samples were homozygotes so that the LOH at this site could not be determined. It should be noticed that, in HCC samples NO.16 and NO.34, there was no LOH at YNZ22 site and D17S1574 site proximal to centromere. In HCC sample NO.16, there was no LOH at D17S34 and D17S1866 sites proximal to centromere. In HCC sample NO.34, there was no LOH at D17S34, D17S1866 and D17S849 sites proximal to centromere. However, in these two HCC samples, all of the sites between D17S849 and D17S1574 had LOH homozygotes. Therefore, the minimum frequent loss region in chromosome 17p13.3 in HCC samples was from D17S849 to D17S1574.

While analyzing the LOH at various sites in chromosome 17p13.3, the LOH of TP53 site in p53 was also analyzed for chromosome 17p13.1. The results showed that said site had only 31% LOH in HCC, much lower than the LOH frequencies of the sites between D17S34 to D17S5 in chromosome 17p13.3 (Tables 1 and 2).

TABLE 1

| | | Probe and LOH | | | | |
|---|---|---|---|---|---|---|
| PROBE | SITE NAME | RESTRICTION ENZYME | PCR ANNEALING TEMP. | NUMBER OF DETECTED HCC SAMPLES | LOH/HETEROZYGOTE NUMBER | % |
| 144D6 | D17S34 | Rsa I | | 21 | 8/12 | 67 |
| | D17S1866* | | 55° C. | 22 | 13/19 | 68 |
| | D17S849* | | 55° C. | 22 | 9/11 | 82 |
| | D17S926* | | 58° C. | 22 | 10/10 | 100 |
| | D17S695* | | 60° C. | 21 | 14/18 | 78 |
| | D17S1840* | | 55° C. | 22 | 6/7 | 86 |
| | D17S1529* | | 60° C. | 33 | 14/17 | 82 |
| | D17S643* | | 60° C. | 22 | 12/16 | 75 |
| | D17S831* | | 60° C. | 31 | 18/24 | 75 |
| | D17S654* | | 65° C. | 22 | 10/13 | 77 |
| | D17S1574* | | 57° C. | 21 | 9/13 | 69 |
| YNH37.3 | D17S28 | TaqI | | 9 | 0/0 | 0 |
| YNZ22 | D17S5 | BamH I | | 22 | 12/19 | 63 |
| | D17S525* | | 59° C. | 12 | 1/4 | 25 |
| cCI17-680 | D17S1587 | Taq I | | 6 | 0/6 | 0 |
| cCI17-708 | D17S878 | Msp I | | 6 | 0/6 | 0 |
| | TP53* | | 60° C. | 22 | 4/13 | 31 |

*microsatellite repeat markers

TABLE 2

LOH Analysis of chromosome 17P13.3 telomere ↑

| probe | Locus | 7 | 12 | 17 | 19 | 26 | 28 | 30 | 95-3 | 54 | 6 | 10 | 16 | 20 | 27 | 31 | 32 | 33 | 34 | 37 | 40 | 59-4 | 25 |
|---|---|---|---|---|---|---|---|---|---|---|---|---|---|---|---|---|---|---|---|---|---|---|---|
| 144D6 | 34 | ● | ● | ⊛ | ● | ● | ● | ● | ● | ● | ● | ⊛ | ⊛ | ○ | ○ | ⊛ | ⊛ | ⊛ | ⊛ | ○ | ○ | ⊛ | ⊛ |
|  | 1866 | ● | ● | ● | ● | ● | ● | ● | ● | ● | ● | ○ | ○ | ○ | ○ | ● | ● | ⊛ | ● | ○ | ⊛ | ○ | ● | ● |
|  | 849 | ⊛ | ● | ● | ⊛ | ⊛ | ⊛ | ⊛ | ⊛ | ⊛ | ⊛ | ○ | ⊛ | ⊛ | ● | ● | ● | ⊛ | ○ | ● | ⊛ | ● | ● |
|  | 926 | ⊛ | ● | ● | ⊛ | ● | ● | ● | ● | ⊛ | ⊛ | ⊛ | ⊛ | ● | ● | ● | ⊛ | ⊛ | ⊛ | ● | ⊛ | ● |
|  | 643 | ● | ● | ● | ● | ● | ● | ● | ● | ● | ○ | ○ | ⊛ | ○ | ⊛ | ● | ● | ● | ● | ⊛ | ○ | ● | ● |
|  | 695 | ⊛ | ● | ● | ● | ⊛ | ● | ● | ● | ● | ○ | ○ | ● | ○ | ● | ● | ● |  | ● | ● | ○ | ● | ● |
|  | 1840 | ⊛ | ⊛ | ● | ● | ● | ● | ⊛ | ⊛ | ⊛ | ○ | ⊛ | ⊛ | ⊛ | ● | ● | ⊛ | ● | ● | ⊛ | ● | ⊛ |
|  | 654 | ⊛ | ● | ● | ● | ⊛ | ● | ● | ● | ⊛ | ○ | ⊛ | ⊛ | ○ | ⊛ | ● | ⊚ | ● | ⊛ | ⊛ | ⊛ | ● | ● |
|  | 1574 | ⊛ | ⊛ | ● | ● | ● | ⊛ | ● | ● | ● | ⊛ | ⊛ | ○ | ○ | ● | ● | ● |  | ○ | ⊛ | ○ | ⊛ | ● |
| YNH37.3 | 28 | ⊛ | ⊛ | ● | ⊛ | ⊛ | ⊛ | ⊛ | ⊛ | ⊛ |  |  |  |  |  |  |  |  |  |  |  |  |  |
| YN222 | 5 | ● | ● | ● | ● | ● | ● | ● | ● | ● | ○ | ○ | ○ | ○ | ○ | ● | ● | ● | ○ | ⊛ | ○ | ⊛ | ⊛ |
|  | 525 | ○ | ○ | ○ | ⊛ | ● | ⊛ | ⊛ | ⊛ | ⊛ | ⊛ | ⊛ | ⊛ |  |  |  |  |  |  |  |  |  |  |
| cC117-680 | 1587 | ○ | ○ | ○ | ○ | ○ | ○ |  |  |  |  |  |  |  |  |  |  |  |  |  |  |  |  |
| cC117-708 | 878 | ○ | ○ | ○ | ○ | ○ | ○ |  |  |  |  |  |  |  |  |  |  |  |  |  |  |  |  |
|  | TP53 | ○ | ⊛ | ⊛ | ● | ○ | ○ | ○ | ● | ⊛ | ○ | ○ | ⊛ | ○ | ● | ⊛ | ⊛ |  | ○ | ⊛ | ○ | ● | ⊛ | centromere

● loss of heterozygosity
○ retention of both alleles
⊛ non-informative
● loss of homozygosity
⊕ rearrangement
space: not analyzed

EXAMPLE 2

Cloning of c63R cDNA

1. Screening genomic PAC clone for D17s926 in chromosome 17p13.3:

The sequences of the D17s926 primers were obtained from Genbank.

```
926-1:   GCA GTG GGC CAT CAT CA    (SEQ ID NO: 3)

926-2:   CCG CAG AAG GCT GTT GT    (SEQ ID NO: 4)
```

The primers were sent to Genome system Inc for screening PAC human genomic library. Positive clone P579 was obtained.

2. A PAC single bacterium was picked from the plate containing P579 (provided by Genome System), inoculated in 5 ml LB containing 25 ug/ml kanamycin and shaken overnight at 37° C., 3000 rpm. 2.5 ml overnight culture was added into 75 ml LB, shaken for 1.5 hr. IPTG was added to final concentration of 0.5 mM. After cultured under induction condition for 5 hr, the bacteria were harvested and centrifuged at 10,000 g for 10 min. The pellet of bacteria was used to prepare PAC DNA according to the method of extraction of plasmid DNA in "Molecular Cloning" (Sambrook, et al., E. F. F.ritsch, T. Maniatis, Translated by Jin Dongyan, Li Menfen, 1992, 2nd edition, Science publication). About 10 ug p579 DNA was obtained.

P579 DNA was digested with Not I at 37° C. for 2–3 hr. The inserts was about 100 Kb. The DNA fragments was recovered from low melting-point gel and used as probes.

200–300 ng of the above purified DNA fragments were labeled with $^{32}$P-α dATP or $^{32}$P-α dCTP in a random priming method according to the specification of the kit (Megaprime DNA labeling system from Amersham).

The bacteriophage solution of cDNA library was plated onto 30 150 mm—diameter Petri dish at 50,000 pfu/plate, and cultured at 41° C. for 3–5 hr. When the diameter of plaques was 0.5 mm and the neighboring plaques were not combined, the Petri dishes were taken out from incubator, placed at 4° C. for at least 1 hr. The plates were taken out from refrigerator and placed in ambient temperature. The NC membrane (Hybond™-C Amersham LIFE Science) was gently placed onto the plate. The injector filled with ink was used to mark 4 points for orientation. The membrane was taken, treated by alkaline denaturation for 5 min (0.5 mol NaOH—1.5 mol NaCl), neutralized for 5 min (1 mol Tris-HCl pH7.4, 1.5 mol NaCl), transferred to 6×SSC, soaked for a while, placed onto 3 mm filtration paper to dry and backed at 80° C. for 2 hr.

The membrane was hybridized in pre-hybridization solution at 65–68° C. for 6–8 hr. The pre-hybridization solution contained 6×SSC, 5×Denhardt's, 0.5% SDS, denatured fish sperm DNA 200 ug/ml, denatured placent DNA 100 ug/ml and mixed DNA (γ DNA 5.8, γ DNA 7.3 and PBR plasmid DNA, 30 ug/ml each).

Into 300 ul solution of labeled probe was added 1 mg Cot-1 DNA and mixed DNA (50 ug each) and 250 ul 20×SSC. The mixture was boiled at 100° C. for 15 min, placed onto ice for 10 min, blocking-hybridized in 60–65° C. water bath for 20 min, and placed onto ice for 20 min. It was added into the pre-hybridization solution containing the membrane and hybridized at 65–68° C. for 16–24 hr. After completion of hybridization, the hybridization solution was discarded and the membrane was rinsed with 42° C. 2×SSC–0.1% SDS solution twice, each for 10 min. During the process of rinse, isotope detector was used for detection so as to adjust the time and temperature for rinsing membranes. After rinse, autoradiography was taken. The same method was used for the 2nd and 3rd round of screening and finally the positive single clone was obtained. The single positive phage was placed into 1 ml SM buffer and a drop of chloroform was added. It was stored at ambient temperature or 4° C. as phage stock of positive single clone. The positive clone of c63R was obtained by said screening.

EXAMPLE 3

Construction of c63R Recombinant Plasmid 100 ul phage stock and bacteria Y1090 cultured overnight and treated with 100 mM $MgSO_4$ were incubated together at 37° C. for 20 min. After addition of 3.5 ml of 0.7% LB agarose (50° C.), the mixture was plated to plate (90 mm diameter) containing 1% agar medium and incubated overnight at 37° C. The plate was taken out, and 3 ml SM solution was added for each plate. After incubation overnight at 4° C., the solution containing phage was collected.

Into 150 ul of said collected phage, 1 ml of strain Y1090 treated with 10 mM $MgSO_4$ was added and incubated at 37° C. for 15 min. 40 ml LB containing 1/100 0.5M $CaCl_2$ was added and vigorously shaken at 37° C. until liquid turned from cloudy to clean (about 3 hr). 1 ml of chloroform was added and at shaken at 37° C. for 20 min, centrifuged at 4000 rpm for 10 min. Into supernatant was added 50 ul of RNAse A/Dnase solution, and incubated at 37° C. for 1 hr. After overnight incubation at 4° C., it was centrifuged at 1000 rpm for 10 min and the supernatant was super-centrifuged at 2700 rpm for 70 min. Into the pellets was added 0.5 ml of SM solution and transferred into 1.5 ml centrifuge tube. 5 ul of proteinase K and 1/5 (v/v) 0.5M STE were added. The mixture was incubated at 50° C. for 30 min, extracted with phenol/chloroform, and precipitated with alcohol to obtain phage DNA. The DNA was digest with EcoR I, and DNA fragments were recovered using gel recovering method (The Gel Recovering Kit was brought from Huasuo Biotechnology Co., Shanghai). The DNA of expression vector PBK-CMV (Stratagene) was digested with same EcoR I and treated with CIAP enzyme. The DNA inserts and vector PBK-CMV DNA in a molar ratio of 3:1 were ligated with T4 DNA ligase at 12° C. overnight, and used to transform competent cell $X_L$I-blue. The white positive clones were picked out for preparation of plasmid DNA. The enzymatic digestion analysis confirmed the subclones were correct.

EXAMPLE 4

Sequencing and Analysis of c63R Nucleic Acid Sequence

The sequencing of the terminal sequence of c63R clones was carried out on ABI 337 DNA auto-sequencer using dideoxy chain termination method. Based on the sequenced sequence, the primers were designed and the sequencing was repeated until the full-length sequence of 2132 bp was obtained. Further analysis showed that the 54 bp at 5' end were from vector. Therefore, the full-length sequence was 2078 bp shown in SEQ ID NO: 1. The ORF was from position 56 to 2077. The full-length c63R protein had 673 amino acid as shown in SEQ ID NO: 2. The combination of nucleic acid and amino acid sequence was shown in SEQ ID NO: 1.

EXAMPLE 5

Gene Cloning from Human cDNA Using PCR

The human liver tissue was taken, and the total RNA was extracted using Trizol™ agents (GIBCO.BRL) according to the specification, and mRNA was extracted using mRNA Purification Kit (Pharmacia). The reverse transcription was carried out at 42 degree using MMLV-RT-Superscript II (GIBCO BRL) to obtain cDNA. The following ORF specific primers were synthesized: c63R-1: atgatggaggaggaggaa (SEQ ID NO: 5); c63R-2: gttgtcacggatgatggg (SEQ ID NO: 6). The protocol was 90° C., 3 min, 1 cycle; 94° C. 30 sec, 60° C. 30 sec, 72° C. 1 min, 35 cycles; 72° C. 10 min, 1 cycles. The amplification product containing complete ORF sequence was obtained. The sequencing confirmed the sequence of the products was in accord with sequence of Example 4.

EXAMPLE 6

Expression of c63R Gene in Various Tissues

The c63R fragment was digested and isolated from c63R recombinant plasmid and labeled with $\alpha^{32}$P-dATP using Kit of Megaprime DNA Labeling System (Amersham) according to the specification. The labeled probes were hybridized with multi-tissue mRNA membrane (Biochain). The results showed that there were 3 hybridization bands in various tissues.

EXAMPLE 7

Alteration of C63R Gene in HCC Tissue

The C63R gene was obtained from chromosome 17p13.3 to further detect the alteration in HCC tissue. The total RNA was extracted from HCC tissues and noncancerous tissues and turned into cDNA by reverse-transcription.

The following C63R specific primers were synthesized:

| C63R-a-PF: | CGGGTGGCGGAATGATG | (SEQ ID NO: 7) |
| C63R-a-PR: | CTCCACCCCCATCTACCA | (SEQ ID NO: 8) |
| C63R-b-PF: | GGTGGCGGAATGATGGA | (SEQ ID NO: 9) |
| C63R-b-PR: | CAAAACGCTTCTCCGGC | (SEQ ID NO: 10) |
| C63R-c-PF: | TGCATGGCTGAGAGGATTG | (SEQ ID NO: 11) |
| C63R-c-PR: | ACAACCCCGTGGCTTCC | (SEQ ID NO: 12) |
| C63R-d-PF: | TGCGTACCAGAGCGAAGG | (SEQ ID NO: 13) |
| C63R-d-PR: | CAAGCAGAACGTCCCCAT | (SEQ ID NO: 14) |
| C63R-a-SR: | AGGATGGACGGCAAGCG | (SEQ ID NO: 15) |
| C63R-b-SR: | GGAGGACCCAGCAATGTT | (SEQ ID NO: 16) |
| C63R-c-SR: | CCAAGACAAGAACCTCGGA | (SEQ ID NO: 17) |
| C63R-d-SR: | AACATCCTGAGCACGGCA | (SEQ ID NO: 18) |

The first PCR was carried out using C63R-a-PF and C63R-a-PR, C63R-c-PF and C63R-c-PR as primers primer and cDNA as template according to the following protocol: 94° C., 3 min, 1 cycle; 94° C., 30 sec (denaturation), 60° C. 30 sec (annealing), 72° C., 1 min (extension), 35 cycles; 72° C., 10 min (extension). The second nested PCR was carried out using C63R-b-PF and C63R-b-PR, C63R-d-PF and C63R-d-PR as primers according to the above protocol, thereby obtaining the PCR products.

The PCR products amplified with primers C63R-b-PF and C63R-b-PR were sequenced with C63R-b-PF, C63R-a-SR, C63R-b-SR, and C63R-b-PR. The PCR products amplified with primers C63R-d-PF and C63R-d-PR were sequenced with C63R-d-PF, C63R-c-SR, C63R-d-SR and C63R-d-PR.

The analysis results showed that in HCC Samples 3, 12, 25, 28, 33 and G11, there were deletion at nt341–427 but there was not corresponding deletion in noncancerous tissue. There was deletion of nt1274–1457 in HCC Sample 28 but there was no corresponding deletion in noncancerous tissue. There was deletion of nt1090–1177 in HCC Sample 31 but there was no corresponding deletion in noncancerous tissue. There was deletion of nt1271–1365 in HCC Sample x31 but there was no corresponding deletion in noncancerous tissue. There was a mutation from C to T at nt1052 in HCC Sample G11, making the amino acid change from Arg to Cys. In HCC Sample G4, there was a deletion of T at nt994, causing frameshift mutation. In HCC Sample GT7, nt743–887 and nt1221–1529 were deleted, causing frameshift mutation. In HCC Sample GT12, nt 1612–1769 was deleted, causing frameshift mutation.

These results indicated that c63R gene was a HCC associated gene. The mutations of c63R gene such as deletion, insertion, and substitution were related to HCC. These mutations made c63R protein have no or low activity in hepatocyte, finally directly or indirectly causing HCC.

EXAMPLE 8

Genomic Structure and Subcellular Location of HCCS1

The exon/intron structure of HCCS1 gene was defined by comparing the cDNA sequences with its genomic sequences. HCCS1 had 18 exons, spanning a genomic sequence of about 200 kb (FIG. 1).

To identify the subcellular localization of the HCCS1 protein product, the HCCS1-GFP fused gene was cloned into pEGFP-N1 vector and the HCCS1-GFP plasmid DNA was transfected into both human HCC cell line SMMC-7721 and mouse NIH/3T3 fibroblasts. The fluorescence image revealed the punctuate distribution of the HCCS1 gene product in the cytoplasm of both types of cells. Overlay of the fluorescence image of GFP and an antimitochondria monoclonal antibody, 113-1 (NeoMarkers, Fremont, Calif.), strongly suggested that HCCS1 fusion protein was located in mitochondria (FIG. 2).

EXAMPLE 9

Immunohistochemical Assays

HCC and noncancerous tissues were fixed in 10% formalin in 10 mM PBS (pH 7.2). The paraffin sections (4 um) were mounted onto poly-L-lysine-coated glass slides and dried overnight at 50° C. Mouse anti-HCCS1 polyclonal antibody was diluted 1:200 in PBS containing 5% normal goat serum and incubated for 30 min at room temperature. After being rinsed in PBS three times for 5 min each, the sections were covered with DAKO EnVision™+System, horseradish peroxidase (3,3'-diaminobenzidine), Mouse Ready-to-use Detection System (DAKO, Carpinteria, Calif.) for 30 min at room temperature. The sections were developed in substrate-chromogen solution (3,3'-diaminobenzidine), counterstained with Mayer's hematoxylin, and mounted.

The results were shown in FIG. 3. The HCC was negative and HC, positive.

EXAMPLE 10

Effect on Cell Growth by HCCS1

According to the manufacturer's protocols, HCCS1 cDNA was inserted into pcDNA3.1/V5-His vector (Invitrogen), and transfected it into SMMC-7721 human hepatic carcinoma cells ($3 \times 10^4$) by using LipofectAMINE in triplicate. Empty vector was used as a control. After G418 (800 mg/ml) selection for 14 days, the colonies were stained and counted.

The results were shown in FIG. 4, indicating HCCS1 inhibited the growth of tumor cells.

EXAMPLE 11

Effect on Formation of Tumor in Nude Mice by HCCS1

Cells harboring HCCS1 cDNA or empty vector were collected and resuspended in PBS. Cells (200 ul; $3.7 \times 10^6$) were inoculated s.c. into the right flank of 5- to 6-week-old male BALB/c nude mice. Experimental and control groups had six mice each. After 5 weeks, mice were sacrificed, and the tumors were dissected and weighed.

The results were shown in FIG. 5, indicating HCCS1 inhibited the formation of tumor in nude mice.

All the documents cited herein are incorporated into the invention as reference, as if each of them is individually incorporated. Further, it would be appreciated that, in the above teaching of the invention, the skilled in the art could make certain changes or modifications to the invention, and these equivalents would still be within the scope of the invention defined by the appended claims of the present application.

What is claimed is:

1. An isolated human c63R polypeptide comprising the amino acid sequence of SEQ ID NO: 2.

2. The polypeptide of claim 1 wherein said polypeptide consists of the amino acid sequence of SEQ ID NO: 2.

3. An isolated polynucleotide comprising a nucleotide sequence selected from the group consisting of:
    (a) the nucleotide sequence encoding the c63R polypeptide of claim 1; and
    (b) a polynucleotide sequence fully complementary to the nucleotide sequence of (a).

4. A kit for amplifying a nucleic acid sequence encoding the polypeptide of claim 1, said kit comprising a primer consisting of the nucleotide sequence of SEQ ID NO: 5 and a primer consisting of the nucleotide sequence of SEQ ID NO: 6.

5. An isolated polynucleotide comprising a nucleotide sequence selected from the group consisting of:
    (a) a nucleotide sequence encoding the human c63R polypeptide of claim 1; and
    (b) a nucleotide sequence fully complementary to the entirety of the nucleotide sequence of (a).

6. A vector containing the DNA sequence encoding the c63R polypeptide of claim 1.

7. An isolated genetically engineered host cell which is selected from the group consisting of:
    (a) a host cell transformed with the vector of claim 6, and
    (b) a host cell transformed with the polynucleotide of claim 3.

8. A method for producing the human c63R protein comprising the amino sequence of SEQ ID NO: 2, which comprises the steps of:
    (a) culturing the host cell of claim 7 under the conditions suitable for the expression of protein;
    (b) isolating the c63R protein from the culture.

9. A method for producing a human c63R protein comprising the amino sequence of SEQ ID NO: 2, which comprises the steps of:
    (a) culturing the host cell of claim 8 or claim 7 under conditions suitable for expression of protein; and
    (b) isolating the human c63R protein from the culture.

10. An isolated polynucleotide comprising a nucleotide sequence selected from the group consisting of:
    (a) the nucleotide sequence of SEQ ID NO: 1; and
    (b) the nucleotide sequence of SEQ ID NO: 1 spanning nucleotides 56–2077.

11. An isolated polynucleotide consisting of a nucleotide sequence selected from the group consisting of:
    (a) the nucleotide sequence of SEQ ID NO: 1; and
    (b) the nucleotide sequence of SEQ ID NO: 1 spanning nucleotides 56–2077.

12. A primer consisting of a nucleotide sequence selected from the group consisting of:
    (a) the nucleotide sequence of SEQ ID NO: 5; and
    (b) the nucleotide sequence of SEQ ID NO: 6.

* * * * *